United States Patent
Yamamoto

(10) Patent No.: US 9,694,146 B2
(45) Date of Patent: Jul. 4, 2017

(54) JOINT MECHANISM

(75) Inventor: Tetsuya Yamamoto, Osaka (JP)

(73) Assignee: SUGAN CO., LTD., Osaka (JP)

( * ) Notice: Subject to any disclaimer, the term of this patent is extended or adjusted under 35 U.S.C. 154(b) by 745 days.

(21) Appl. No.: 14/004,573

(22) PCT Filed: Mar. 11, 2011

(86) PCT No.: PCT/JP2011/055812
§ 371 (c)(1),
(2), (4) Date: Sep. 11, 2013

(87) PCT Pub. No.: WO2012/124028
PCT Pub. Date: Sep. 20, 2012

(65) Prior Publication Data
US 2013/0340608 A1    Dec. 26, 2013

(51) Int. Cl.
| | |
|---|---|
| *A61M 5/50* | (2006.01) |
| *A61M 5/315* | (2006.01) |
| *F04B 1/00* | (2006.01) |
| *A61M 5/145* | (2006.01) |
| *F04B 13/00* | (2006.01) |
| *F04B 53/14* | (2006.01) |

(52) U.S. Cl.
CPC ...... *A61M 5/5066* (2013.01); *A61M 5/31515* (2013.01); *A61M 5/14546* (2013.01); *A61M 5/14566* (2013.01); *F04B 1/00* (2013.01); *F04B 13/00* (2013.01); *F04B 53/14* (2013.01)

(58) Field of Classification Search
CPC ............ A61M 5/31515; A61M 5/5066; A61M 5/14546
See application file for complete search history.

(56) References Cited

U.S. PATENT DOCUMENTS

| | | | |
|---|---|---|---|
| 4,677,980 A | 7/1987 | Reilly et al. | |
| 5,084,017 A * | 1/1992 | Maffetone | A61M 5/5066 604/110 |
| 5,090,962 A * | 2/1992 | Landry, Jr. | A61M 5/31511 604/110 |

(Continued)

FOREIGN PATENT DOCUMENTS

| | | |
|---|---|---|
| CN | 1251049 A | 4/2000 |
| CN | 201030119 Y | 3/2008 |

(Continued)

OTHER PUBLICATIONS

International Search Report in PCT/JP2011/055812 dated Apr. 19, 2011 with English Translation.

(Continued)

*Primary Examiner* — Theodore Stigell
*Assistant Examiner* — Benjamin Koo
(74) *Attorney, Agent, or Firm* — McDermott Will & Emery LLP

(57) ABSTRACT

In the joint mechanism, when connecting a plunger to a piston, after engaging members of a plunger-side engaging region in a retracted state pass through a first engaging wall region of a piston-side engaging region, the engaging members of the plunger-side engaging region come into a projected state in a second engaging wall region and the projected state of the engaging members is fastened by a fast block, and thereby, the plunger-side engaging region engages with the piston-side engaging region.

2 Claims, 8 Drawing Sheets

(56) References Cited

U.S. PATENT DOCUMENTS

| | | | | |
|---|---|---|---|---|
| 7,419,478 B1* | 9/2008 | Reilly | .............. | A61M 5/14546 |
| | | | | 604/218 |
| 7,682,345 B2* | 3/2010 | Savage | ................ | A61M 5/007 |
| | | | | 604/151 |
| 2014/0094749 A1* | 4/2014 | Cowan | ................. | A61M 5/315 |
| | | | | 604/93.01 |

FOREIGN PATENT DOCUMENTS

| | | |
|---|---|---|
| EP | 1849490 A1 | 10/2007 |
| JP | 2004-290352 A | 10/2004 |
| WO | 98/43690 A1 | 10/1998 |
| WO | 2006/087762 A1 | 8/2006 |

OTHER PUBLICATIONS

Chinese Office Action dated Nov. 4, 2014 issued in Chinese Application No. 201180069185.6 (Partial English translation).

\* cited by examiner (A)  (B)

JOINT MECHANISM

RELATED APPLICATIONS

This application is the U.S. National Phase under 35 U.S.C. §371 of International Application No. PCT/JP2011/055812, filed on Mar. 11, 2011, the disclosure of which Application is incorporated by reference herein.

TECHNICAL FIELD

The present invention relates to a joint mechanism, and in particular relates to a joint mechanism for a slidable plunger in an injector head and a piston which is disposed inside a syringe mounted on the injector head.

BACKGROUND ART

In the field of medicine, injector heads have been used in angiographic examinations to deliver contrast agents into blood vessels of patients. The injector head is disposed with a plunger which is controlled to be slidable in an antero-posterior direction. The injector head is mounted with a syringe having a substantially cylindrical shape. Moreover, a piston to be connected to the plunger is disposed inside the syringe.

In a state where the syringe is mounted on the injector head, the plunger and the piston are connected, and as the plunger is moved forward, the piston is forced by the plunger to move forward to deliver a liquid medicine, a contrast agent or the like housed in the syringe into the blood vessel of a patient. By moving the plunger backward, it is possible to refill a liquid medicine, a contrast agent or the like into the syringe.

Such joint mechanism for a plunger and a piston has been disclosed by, for example, Japanese Patent Laying-Open No. 2004-290352 (PTD 1) and U.S. Pat. No. 4,677,980 (PTD 2).

CITATION LIST

Patent Document

PTD 1: Japanese Patent Laying-Open No. 2004-290352
PTD 2: U.S. Pat. No. 4,677,980

SUMMARY OF INVENTION

Technical Problem

In recent years, in addition to high performance, the injector head has been strongly required to be made compact in size. Therefore, there comes the necessity for the joint mechanism for the plunger and the piston to satisfy the compact-size requirement. Therefore, an object of the present invention is to provide a joint mechanism having a structure which enables the joint mechanism for a plunger and a piston to be made compact in size.

Solution To Problem

The joint mechanism according to the present invention is used to connect a slidable plunger disposed in an injector head and a piston which is disposed inside a syringe mounted on the injector head. A plunger-side engaging region which engages with the piston is disposed at a front end of the plunger, and a piston-side engaging region which engages with the plunger-side engaging region is disposed inside the piston.

The piston-side engaging region includes a first engaging wall region having a first inner diameter, and a second engaging wall region located inside relative to the first engaging wall region and having a second inner diameter larger than the first inner diameter.

The plunger-side engaging region includes a cylindrical portion having an outer diameter smaller than the first inner diameter, an engaging member disposed inside the cylindrical portion in a way of being switchable between a projected state of projecting from an outer surface of the cylindrical portion and a retracted state without projecting from the outer surface of the cylindrical portion, and a fast block for fastening the projected state of the engaging member. The fast block is disposed inside the cylindrical portion and closer to the center side thereof than the engaging member.

In the case where the plunger and the piston are in a connected state, the fast block prevents the engaging member from moving toward a center side in a radial direction so as to fasten the engaging member in the projected state, and in the case where the plunger and the piston are in a disconnected state, the prevention by the fast block of the movement of the engaging member toward the center side in the radial direction is released.

In another aspect, the fast block is formed into a shape of a substantially equilateral triangle, the engaging member is disposed on a peripheral surface of the cylindrical portion at three locations with a pitch of 120° and is configured to be rotatable around the fast block together with the cylindrical portion, the projected state of the engaging member is fastened at a position where three vertices of the triangle of the fast block come into contact with an inner side of the engaging member, and the fastening of the projected state of the engaging member is released at a position where the engaging member is rotated by 60° to disengage the three vertices of the triangle of the fast block from the inner side of the engaging member.

In another aspect, the engaging member includes a projected portion projectable from an outer surface of the cylindrical portion, an extended portion extending from the projected portion in an axial direction of the cylindrical portion, and a base portion disposed at a side of the extended portion which is opposite to the projected portion. Three base portions are formed into a circular shape by combining the three base portions of the three engaging members together and having a fast ring disposed around outer peripheral surfaces of the base portions.

In another aspect, the fast block, as a whole, is formed into a shape of a race track having a curved surface portion and a linear portion which is configured to include a pair of D-cut surfaces each having a flat face on a part of the peripheral surface of a circular block. The engaging member is disposed on a peripheral surface of the cylindrical portion at two locations with a pitch of 180° and is configured to be rotatable around the fast block together with the cylindrical portion. The projected state of the engaging member is fastened at a position where two vertices of the curved surface portions of the fast block come into contact with an inner side of the engaging member, and the fastening of the projected state of the engaging member is released at a position where the engaging member is rotated by 90° to disengage the two vertices of the fast block from the inner side of the engaging member.

In another aspect, the engaging member includes a projected portion projectable from an outer surface of the cylindrical portion, an extended portion extending from the projected portion in an axial direction of the cylindrical portion, and a base portion disposed at a side of the extended portion which is opposite to the projected portion. Two base portions are formed into a circular shape by combining the two base portions of the two engaging members together and having a fast ring disposed around outer peripheral surfaces of the base portions.

In another aspect, the engaging member is normally retained at the projected state, and as the engaging member passes through the first engaging wall region of the piston-side engaging region, the retracted state without projecting from the outer surface of the cylindrical portion is selected.

Advantageous Effects Of Invention

According to the joint mechanism of the present invention, it is possible to make the joint mechanism for the plunger and the piston compact in size.

BRIEF DESCRIPTION OF DRAWINGS

FIG. 9(A) is a view illustrating the relationship between the engaging member and the fast block, and FIG. 9(B) is a partial sectional view illustrating the positional relationship between the plunger and the piston;

FIG. 10(A) is a view illustrating the relationship between the engaging member and the fast block, and FIG. 10(B) is a partial sectional view illustrating the positional relationship between the plunger and the piston;

FIG. 11(A) is a view illustrating the relationship between the engaging member and the fast block, and FIG. 11(B) is a partial sectional view illustrating the positional relationship between the plunger and the piston;

FIG. 12(A) is a view illustrating the relationship between the engaging member and the fast block, and FIG. 12(B) is a partial sectional view illustrating the positional relationship between the plunger and the piston;

FIG. 13(A) is a view illustrating the relationship between the engaging member and the fast block, and FIG. 13(B) is a partial sectional view illustrating the positional relationship between the plunger and the piston;

DESCRIPTION OF EMBODIMENTS

Figure 1:
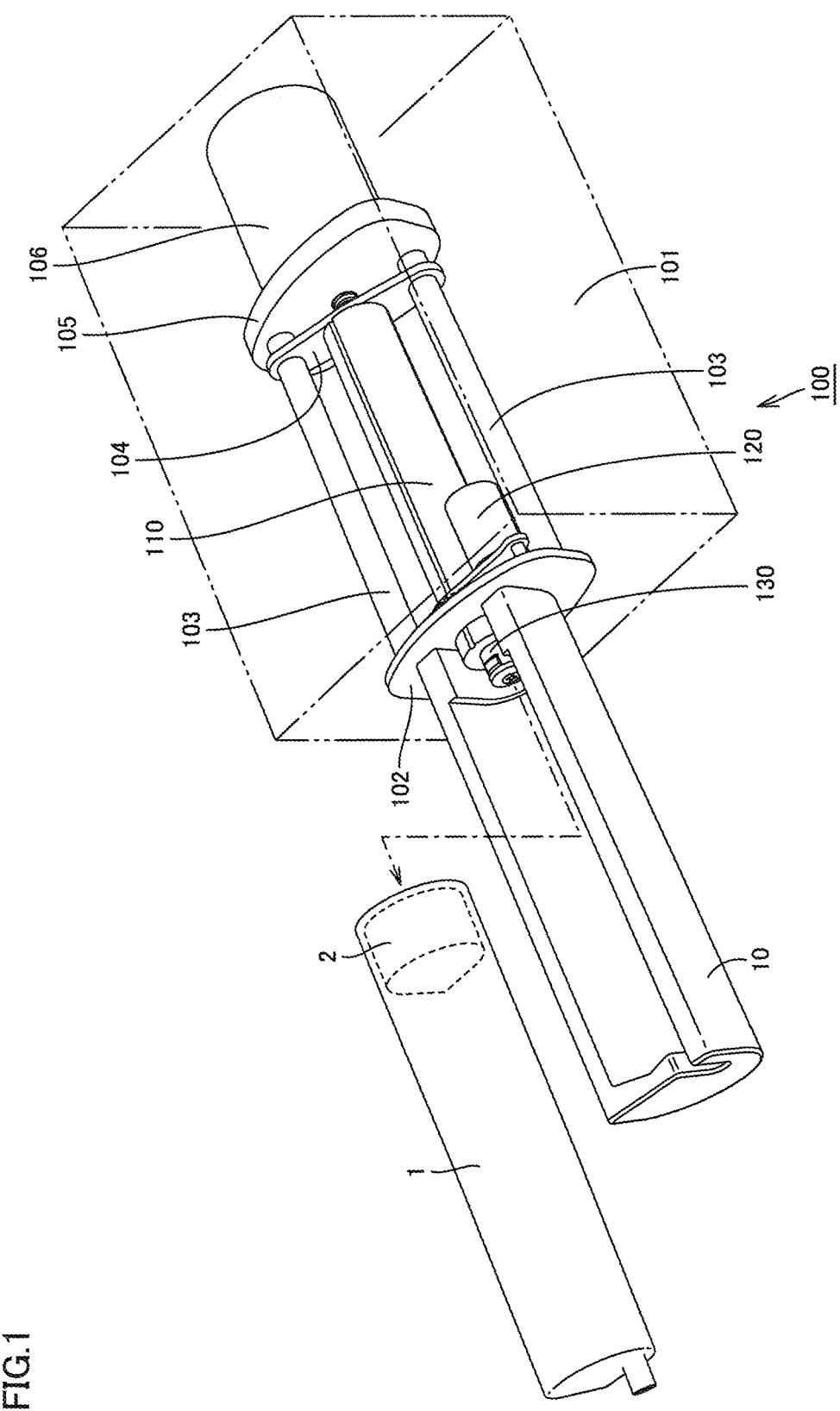
FIG. 1 is an overall perspective view illustrating a schematic mechanism of an injector head according to an embodiment.

Hereinafter, a joint mechanism of the present invention will be described. In the following embodiments, the description is carried out in the case where the joint mechanism of the present invention is adopted as an application example in a connection between a slidable plunger disposed in an injector head and a piston which is disposed inside a syringe mounted on the injector head to be used in a contrast agent delivery system in a medical field; however, it is also possible to adopt the joint mechanism of the present invention in other locations needing a similar connection in the medical field.

It should be noted that in the drawings mentioned below, the same or corresponding portions are given the same reference characters and the description thereof may not repeated. In the case where the numbers, the amount and the like are referred to, unless otherwise indicated, the scope of the present invention is not necessarily limited to the numbers, the amount and the like.

(Injector Head)

With reference to FIG. 1, an injector head 100 of the present embodiment and a syringe 1 mounted on injector head 100 will be described. FIG. 1 is an overall perspective view illustrating a schematic mechanism of injector head 100 of the present embodiment.

Injector head 100 includes a housing 101 which houses therein major equipment, a front plate 102 mounted on a front surface of housing 101, and a pressure jacket 10 fixed on front plate 102.

Pressure jacket 10 holds syringe 1 mounted on injector head 100, and meanwhile inhibits the expansion of injector head 100 which occurs as an increasing pressure is applied to injector head 100. A piston 2 is disposed inside syringe 1 for sealing an interior space therein.

An opening is provided in front plate 102, and a plunger 110 is controlled to move forward or backward through the opening by the major equipment housed in housing 101. A pair of spacer rods 103, an end plate 104, a base block 105, a plunger forward-backward movement controlling servo motor 106, and a piston-plunger connection-control stepping motor 120 are housed in housing 101.

(Internal Mechanism of Injector Head 100)

Figure 2:
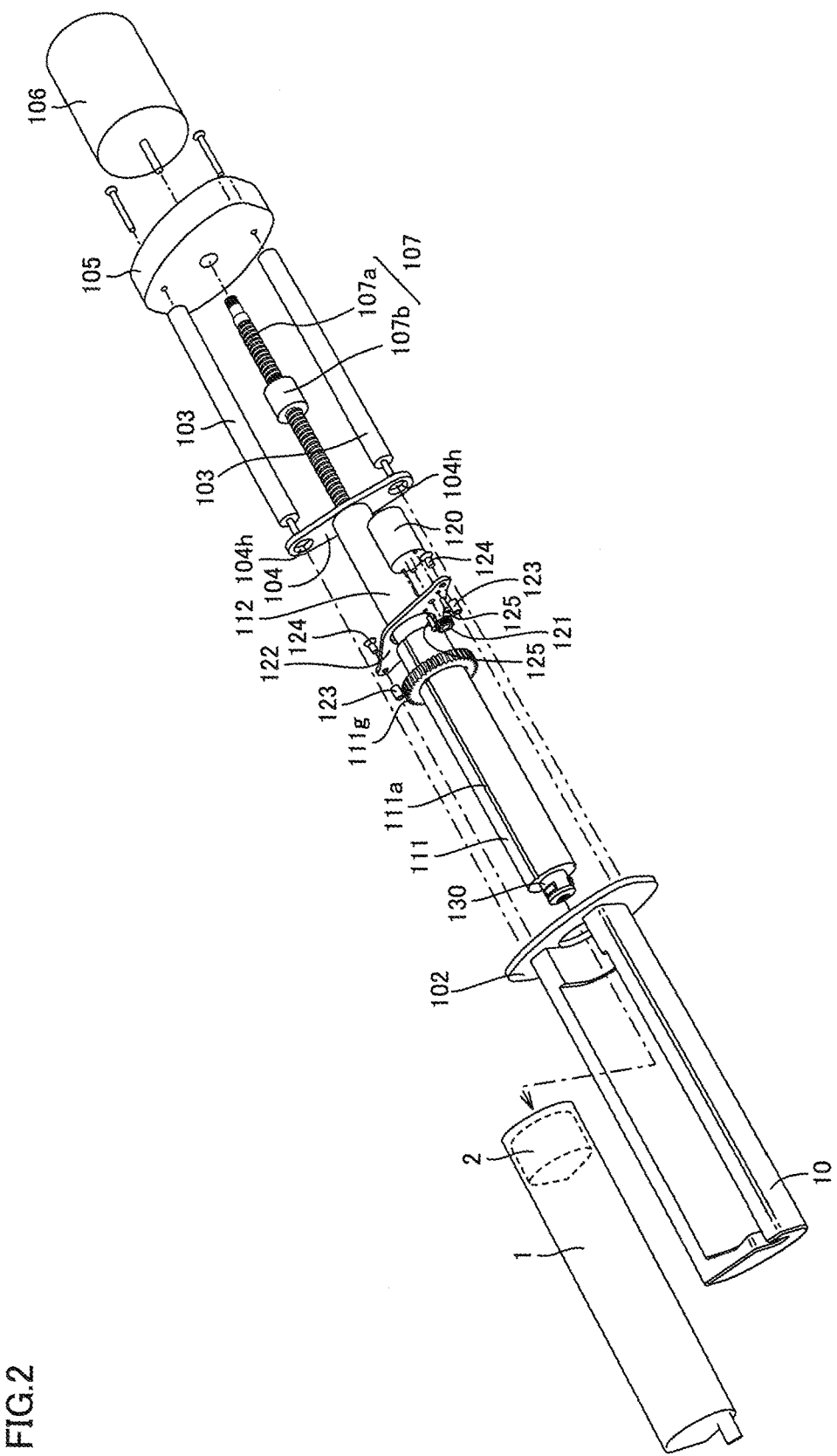
FIG. 2 is an exploded perspective view illustrating an internal mechanism of the injector head according to an embodiment.

Hereinafter, with reference to FIG. 2, the detailed structure of the major equipment housed in housing 101 will be described. FIG. 2 is an exploded perspective view illustrating the internal mechanism of injector head 100. Plunger 110 has an outer cylinder 111 having a plunger-side engaging region 130 formed at a proximal end thereof. The outer surface of outer cylinder 111 is formed with a groove 111a extending in the axial direction. The detailed structure of plunger-side engaging region 130 will be described later.

A slider 112 is housed inside outer cylinder 111. A proximal end of slider 112 is disposed with a fast pin 113, and end plate 104 is fixed to a rear end of slider 112. End plate 104 is long in the lateral direction and is disposed with a slide hole 104h allowing spacer rod 103 to pass through.

A ball screw 107 is housed inside slider 112. Ball screw 107 includes a screw shaft 107a which is coupled to plunger forward-backward movement controlling servo motor 106, and a nut 107b which is screwed on screw shaft 107a and fixed to slider 112.

The movement of screw shaft 107a is controlled by plunger forward-backward movement controlling servo motor 106 through controlling the rotation of screw shaft 107a, and thereby, plunger 110 is controlled to move forward-backward.

Further, the outer peripheral surface of outer cylinder 111 is provided with a rack gear 111g engaging with groove 111a. A pinion gear 121 connected to connection-control stepping motor 120 is screwed on rack gear 111g. A rotation angle of outer cylinder 111 around slider 112 is controlled through controlling the rotation of connection-control stepping motor 120.

In addition, the rotation angle control is not limited to using connection-control stepping motor 120, and it is possible to perform the rotation angle control through belt driving.

Plunger forward-backward movement controlling servo motor 106 is supported by base block 105. Connection-control stepping motor 120 is fixed on a holding plate 122 through the use of a screw 125. Holding plate 122 is fixed on front plate 102 through screws 124 with a spacer 123 interposed therebetween.

(Plunger-Side Engaging Region 130)

Figure 3:
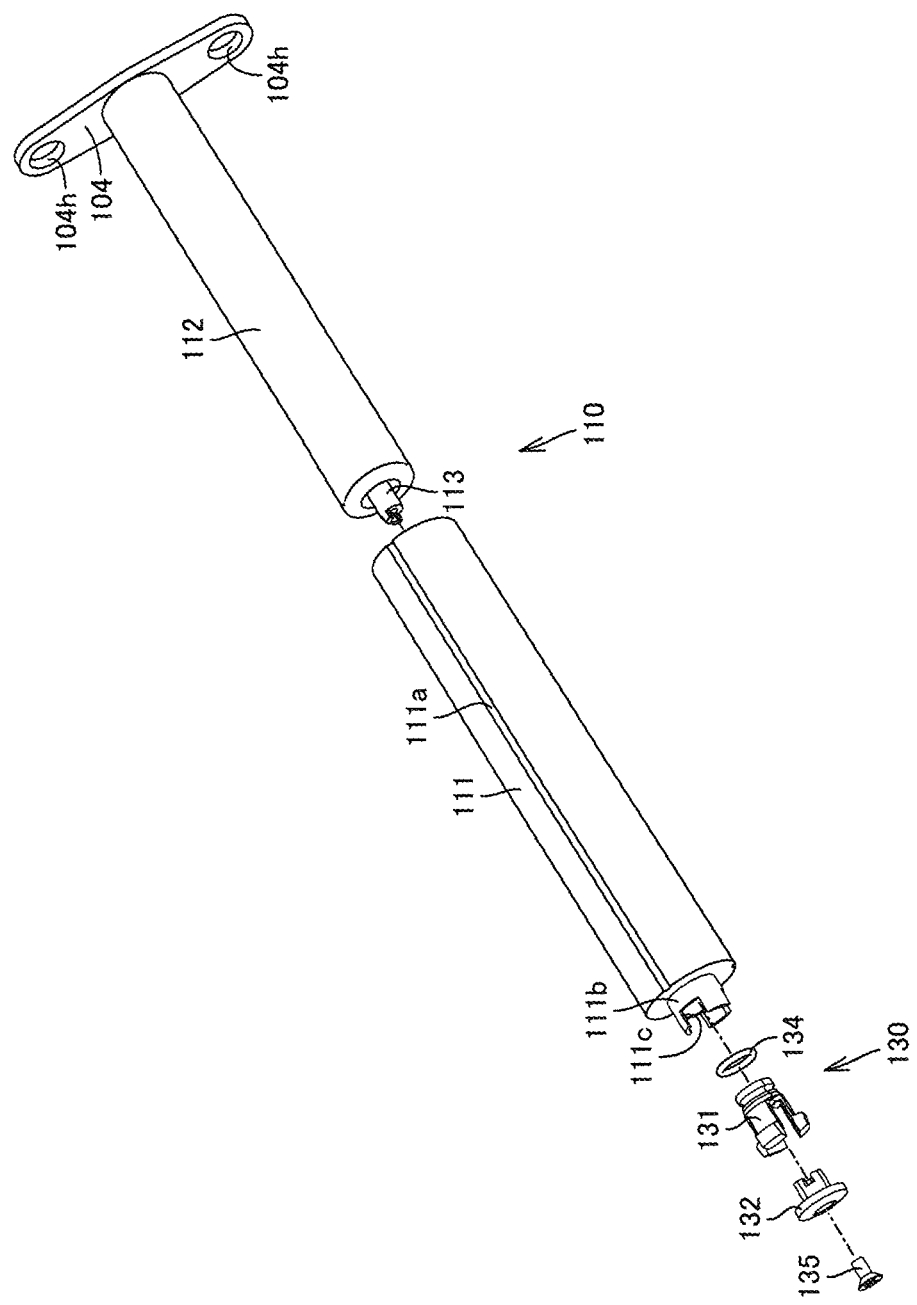
FIG. 3 is an exploded perspective view illustrating a structure of a plunger according to an embodiment.
Figure 5:
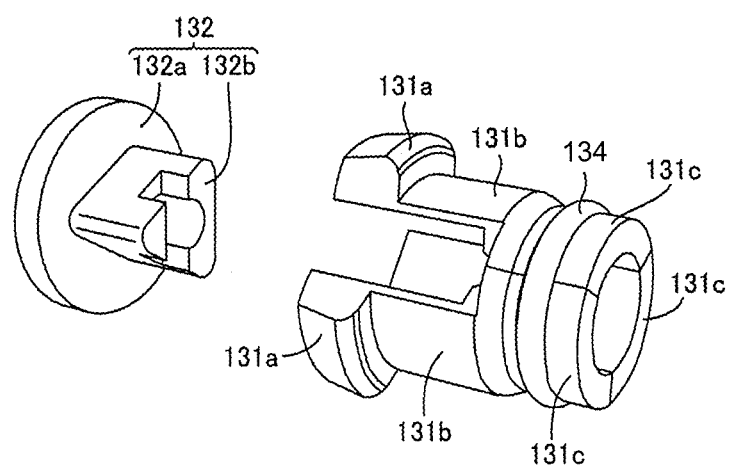
FIG. 5 is a perspective view illustrating the structure of the fast pin and the structure of the engaging member in an assembled state according to an embodiment.
Figure 6:
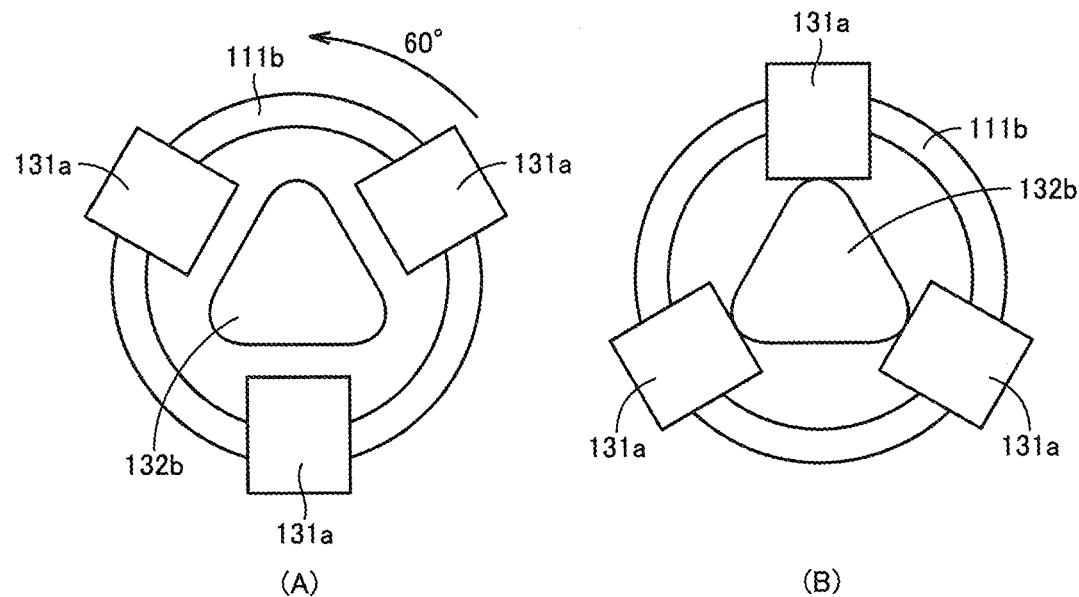
FIG. 6(A) is a schematic view illustrating an unfastened state of projected portions of the engaging member by a fast block.
FIG. 6(B) is a schematic view illustrating a fastened state of projected portions of the engaging member by the fast block.

Hereinafter, with reference to FIGS. 3 to 6, the detailed structure of plunger-side engaging region 130 will be described. FIG. 3 is an exploded perspective view illustrating a structure of plunger 110, FIG. 4 is an exploded perspective view illustrating a structure of a fast member 132 and an engaging member 131, FIG. 5 is a perspective view illustrating a structure of fast member 132 and a structure of engaging member 131 in an assembled state, FIG. 6(A) is a schematic view illustrating an unfastened state of projected portions of the engaging member by a fast block, and FIG. 6(B) is a schematic view illustrating a fastened state of projected portions of the engaging member by the fast block.

Figure 4:
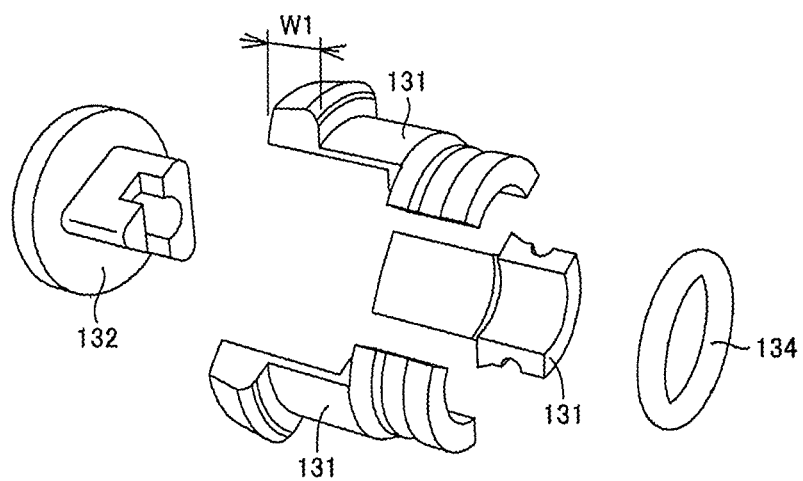
FIG. 4 is an exploded perspective view illustrating a structure of an engaging member and a fast pin according to an embodiment.

With reference to FIGS. 3 and 4, a proximal end of outer cylinder 111 is disposed with a cylindrical portion 111b projecting toward the proximal end. Cylindrical portion 111b has an outer diameter smaller than a first inner diameter (D1) of a first engaging wall region 21 of a piston-side engaging region 20 disposed in piston 2 which will be described later (see FIGS. 7 and 8).

Further, cylindrical portion 111b is disposed with a window region 111c having a predetermined opening area at three locations in total with a pitch of 120°. Window region 111c allows a projected portion 131a of engaging member 131 which will be described later to project from the outer peripheral surface of cylindrical portion 111b.

Three engaging members 131 are disposed inside cylindrical portion 111b. Each engaging member 131 in each window region 111c disposed in cylindrical portion 111b includes projected portion 131a capable of projecting from the outer surface of cylindrical portion 111b, an extended portion 131b extending from projected portion 131a in the axial direction of cylindrical portion 111b, and a base portion 131c disposed at a side of extended portion 131b which is opposite to projected portion 131a. Engaging member 131 is made of a resin material or a metal material.

As illustrated in FIG. 5, base portions 131c of three engaging members 131 are combined together, and a fast ring 134 is disposed on the outer peripheral surface of base portions 131c, and thereby, three base portions 131c are formed into a circular shape.

Figure 10:
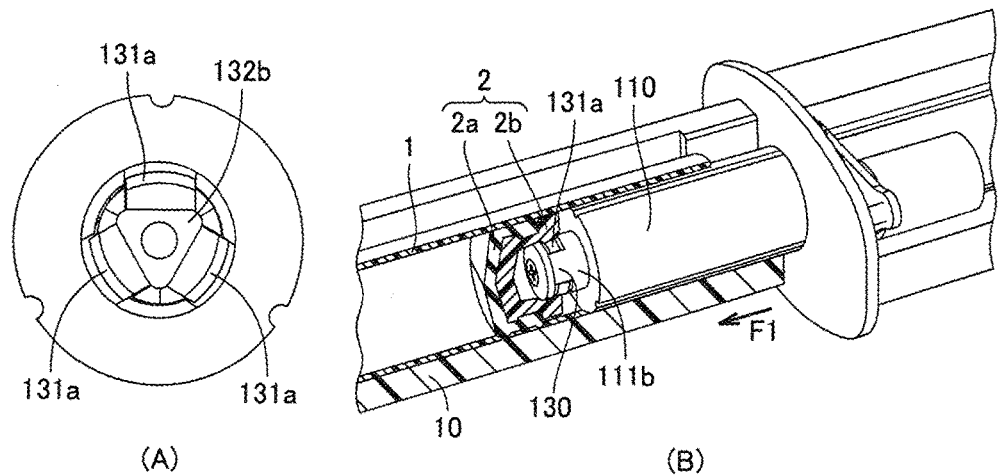
FIG. 10 is a second view illustrating connection operations of the injector head according to an embodiment.
Figure 11:
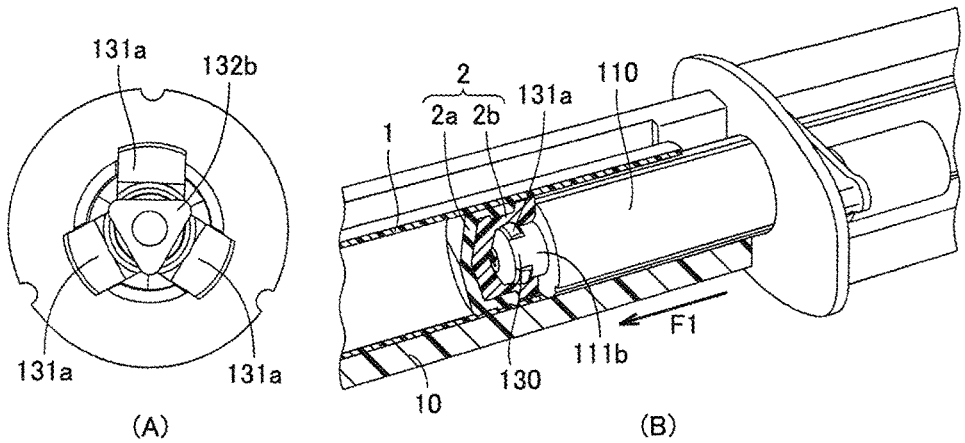
FIG. 11 is a third view illustrating connection operations of the injector head according to an embodiment.
Figure 12:
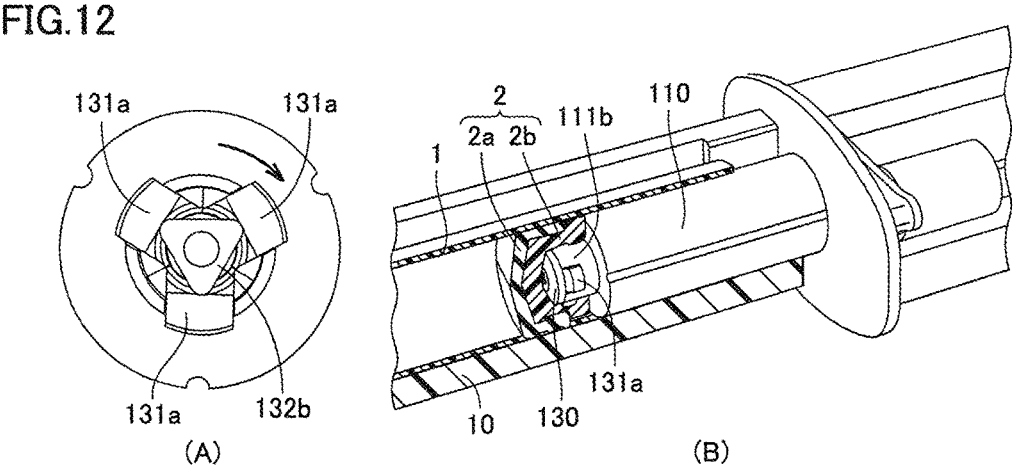
FIG. 12 is a fourth view illustrating connection operations of the injector head according to an embodiment.
Figure 13:
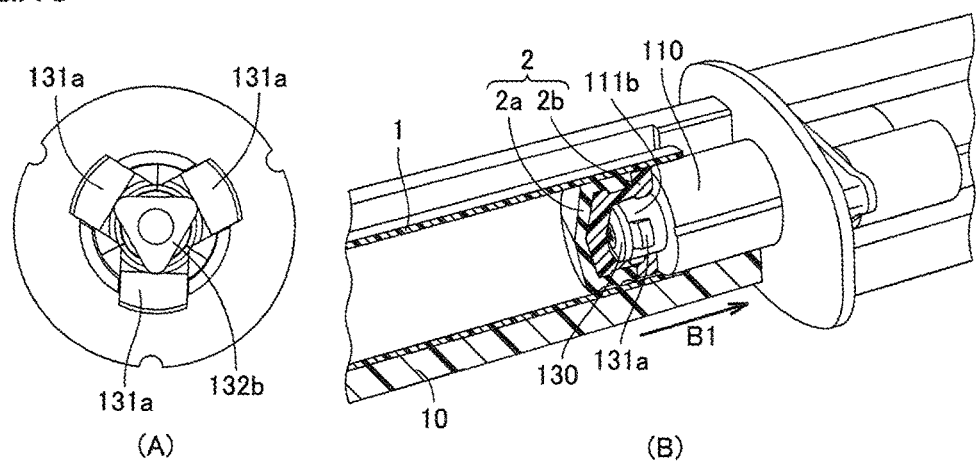
FIG. 13 is a fifth view illustrating connection operations of the injector head according to an embodiment.

In the case where an external force is applied from the external side to projected portions 131a toward the central portion in the radial direction (see the states in FIG. 10(A) and FIG. 10(B) to be described later), projected portions 131a displace toward the central portion into a retracted state in which projected portions 131a do not project from the outer surface of cylindrical portion 111b. In this case, fast ring 134 deforms elastically by expanding in the radial direction, allowing projected portions 131a to displace toward the central portion. In the case where the external force applied to projected portions 131a is released, projected portions 131a restore to the state as illustrated in FIG. 5 based on a biasing force from fast ring 134.

Three engaging members 131 combined together by fast ring 134 are fixed inside cylindrical portion 111b in a way of being sandwiched by fast member 132 and fast pin 113.

Fast member 132 includes a fast plate 132a having an outer diameter capable of occluding an open end of cylindrical portion 111b, and a fast block 132b which is connected to fast plate 132a. As illustrated in FIG. 3, fast member 132 is fixed to a front end of fast pin 113 through the use of a screw 135. Fast block 132b is located in the center when viewed from projected portions 131a.

At this time, since fast member 132 is fastened to fast pin 113, fast member 132 cannot rotate. On the other hand, three combined engaging members 131 can rotate together with outer cylinder 111 which rotates around slider 112.

Fast block 132b is designed into a substantially equilateral triangle shape, and three vertices are processed to have a predetermined curved surface to offer a smooth contacting slide on an inner surface of projected portions 131a of engaging member 131.

Hereinafter, with reference to FIGS. 6(A) and FIG. 6(B), the positional relationship among cylindrical portion 111b, projected portions 131a of engaging member 131 and fast block 132b will be described. Under the rotation control by connection-control stepping motor 120, cylindrical portion 111b rotates together with outer cylinder 111 and projected portions 131a rotate together with cylindrical portion 111b.

As illustrated in FIG. 6(A), projected portions 131a are normally retained at a projected state of projecting from cylindrical portion 111b. In the case where projected portions 131a are located at positions facing the sides of the triangle of fast block 132b, a gap is formed between each projected portion 131a and fast block 132b, and in the case where an external force is applied to projected portions 131a from the external side toward the central portion in the radial direction, projected portions 131a displace toward the central portion into the retracted state in which projected portions 131a do not project from the outer surface of cylindrical portion 111b.

On the other hand, as illustrated in FIG. 6(B), in a state where cylindrical portion 111b and projected portions 131a are rotated by 60° relative to fast block 132b, three vertices of the triangle of fast block 132b come into contact with the inner side of projected portions 131*a*, and projected portions 131*a* are fastened in the projected state.

(Piston 2)

Figure 7:
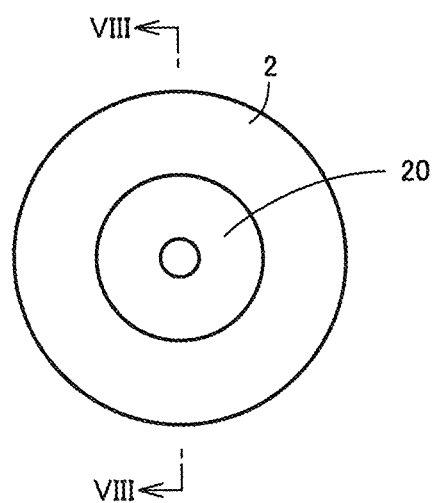
FIG. 7 is a plan view illustrating a piston according to an embodiment.
Figure 8:
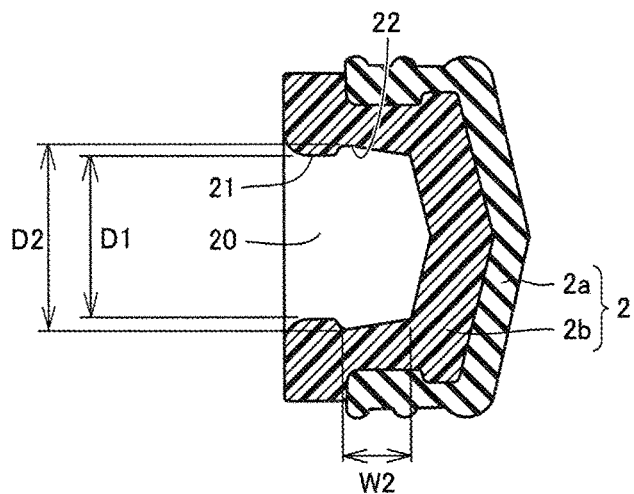
FIG. 8 is a cross sectional view taken along a line VIII-VIII in FIG. 7.
Figure 9:
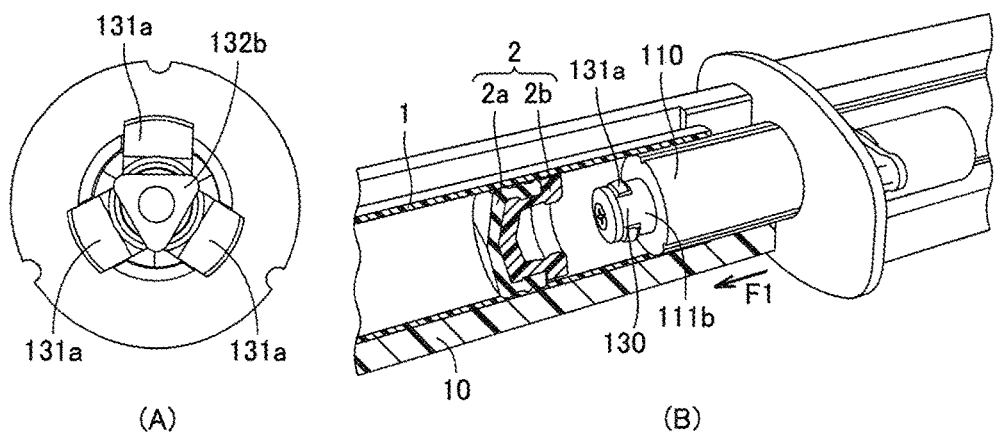
FIG. 9 is a first view illustrating connection operations of the injector head according to an embodiment.

Hereinafter, with reference to FIGS. 7 and 8, the shape of piston 2 will be described. FIG. 7 is a plan view illustrating piston 2, and FIG. 8 is a cross sectional view taken along a line VIII-VIII in FIG. 7. Piston 2 includes a piston rubber 2*a* and a piston core 2*b*. The abovementioned piston-side engagement region 20 which engages with plunger-side engagement region 130 is disposed inside piston core 2*b*.

Piston-side engagement region 20 includes first engaging wall region 21 having the first inner diameter (D1) and a second engaging wall region 22 located inside (closer to the proximal end) relative to first engaging wall region 21 and having a second inner diameter larger than the first inner diameter (D1).

Referring again to FIG. 6(A) and FIG. 6(B), in the case where projected portions 131*a* and fast block 132*b* are in the normal state as illustrated in FIG. 6(A) and cylindrical portion 111*b* of plunger-side engagement region 130 has entered into first engaging wall region 21, after fast block 132*b* comes into contact with first engaging wall region 21, it is pushed to displace toward the central portion, which allows cylindrical portion 111*b* to pass through first engaging wall region 21.

After cylindrical portion 111*b* of plunger-side engaging region 130 has passed through first engaging wall region 21, cylindrical portion 111*b* restores to the state of FIG. 6(A) in second engaging wall region 22. Thereafter, as illustrated in FIG. 6(B), when fast block 132*b* is rotated by 60° relative to fast block 132*b*, three vertices P1 of the triangle of fast block 132*b* come into contact with the inner side of projected portions 131*a*, and thereby, projected portions 131*a* are fastened at the projected state.

Consequently, projected portions 131*a* inside piston-side engaging region 20 engage with a step portion formed by first engaging wall region 21 and second engaging wall region 22, and plunger-side engaging region 130 is fastened to piston-side engaging region 20.

(Connection Operations of Injector Head)

Hereinafter, with reference to FIGS. 9 to 13, the connection operations of the injector head will be described. FIGS. 9 to 13 are first to fifth drawings illustrating the connection operations of the injector head, in which (A) is a view illustrating the relationship between the fast block and the engaging member, and (B) is a partial cross sectional view illustrating the positional relationship between the piston and the plunger.

With reference to FIG. 9(B), after syringe 1 is mounted in plunger jacket 10, plunger 110 is moved forward (in the arrow direction of F1 in FIG. 9(B)). In this state, as illustrated in FIG. 9(A), projected portions 131*a* are located at positions facing to the sides of the triangle of fast block 132*b*, and a gap is formed between projected portions 131 and fast block 132*b*.

Thereafter, with reference to FIG. 10(B), plunger 110 is moved further forward (in the arrow direction of F1 in FIG. 10(B)). In this state, since cylindrical portion 111*b* of plunger-side engaging region 130 has entered first engaging wall region 21, projected portions 131*a* come into contact with first engaging wall region 21 of piston 2, and thereby, an external force is applied to projected portions 131*a* from the external side toward the central portion in the radial direction. Thus, as illustrated in FIG. 10(A), projected portions 131*a* displace toward the central portion into the retracted state in which projected portions 131*a* do not project from the outer surface of cylindrical portion 111*b*.

Then, with reference to FIG. 11(B), plunger 110 is moved further forward (in the arrow direction of F1 in FIG. 10(B)). In this state, since cylindrical portion 111*b* of plunger-side engagement region 130 has entered second engaging wall region 22, first engaging wall region 21 is released from contacting with projected portions 131*a*. Thus, as illustrated in FIG. 11(A), projected portions 131*a* restore to the same state as in FIG. 9(A).

Thereafter, with reference to FIG. 12(B), plunger 110 is rotated axially by 60°. At this time, since fast block 132*b* is in the fastened state, as illustrated in FIG. 12(A), three vertices P1 of the triangle of fast block 132*b* come into contact with the inner side of projected portions 131*a*, and projected portions 131*a* are fastened in the projected state. Thus, projected portions 131*a* inside piston-side engaging region 20 engage with the step portion formed by first engaging wall region 21 and second engaging wall region 22, and plunger-side engaging region 130 is fastened to piston-side engaging region 20.

Next, with reference to FIG. 13(B), in the case where plunger 110 is moved backward (in the arrow direction of B1 in FIG. 13(B)), since piston-side engaging region 20 is in engagement with plunger-side engaging region 130, it is possible to move piston 2 to follow the movement of plunger 110. The same applies to the case where plunger 110 is moved forward.

As mentioned above, in the joint mechanism for plunger 110 and piston 2 according to the present embodiment, since a mechanism for engaging plunger-side engaging region 130 with piston-side engaging region 20 disposed inside piston 2 is adopted, it is possible to house the connection mechanism inside piston 2. Thereby, it is possible to make the joint mechanism compact in size.

Moreover, in the case where the width (W1) of projected portion 131*a* in the axial direction as illustrated in FIG. 4 is made substantially identical to the width (W2) of second engaging wall region 22 of piston 2 as illustrated in FIG. 8, it is possible to house projected portions 131*a* inside second engaging wall region 22 without leaving any gap. As a result, in moving plunger 110, it is possible to move piston 2 without any play (i.e., piston 2 is fixed).

Thereby, even in the case where plunger 110 is switched to move from a suction direction to a delivery direction after a liquid medicine or the like is sucked into syringe 1, since there is no play between plunger 110 and piston 2, it is possible to deliver the liquid medicine or the like at a precise amount.

Figure 14:
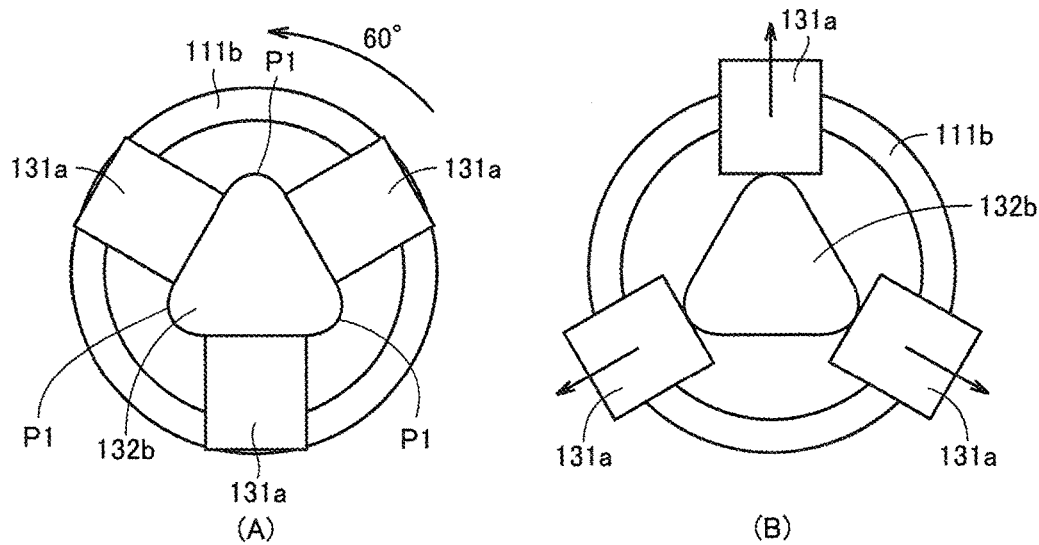
FIG. 14(A) is a schematic view illustrating an unfastened state of the projected portions of the engaging member by the fast block and FIG. 14(B) is a schematic illustrating a fastened state of the projected portions of the engaging member by the fast block according to another embodiment.

In the above embodiments, engaging member 131 has been described in connection with the case where projected portions 131*a* are normally retained at the projected state of projecting from cylindrical portion 111*b* as illustrated in FIG. 6(A), but it is not limited thereto. For example, it is possible that normally projected portions 131*a* are housed inside cylindrical portion 111*b* and retained at a state of contacting the side of the triangle of fast block 132*b* as illustrated in FIG. 14(A), and in the case where cylindrical portion 111*b* and projected portions 131*a* are rotated by 60° relative to fast block 132*b* as illustrated in FIG. 14(B), three vertices P1 of the triangle of fast block 132*b* come into contact with the inner side of projected portions 131*a*, projected portions 131*a* are pushed outward in the radial direction and thereby fastened in the projected state.

Figure 15:
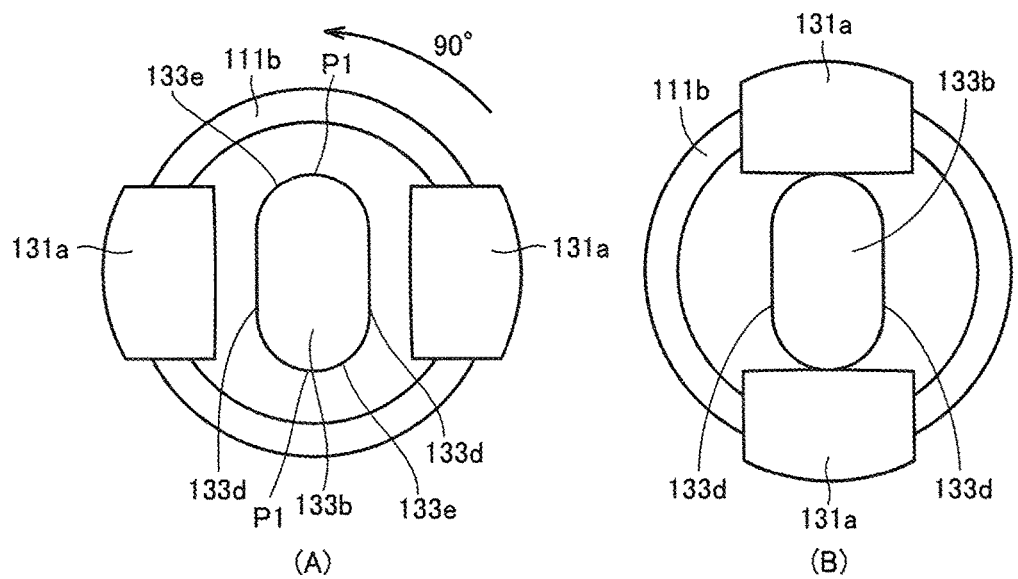
FIG. 15(A) is a schematic view illustrating an unfastened state of the projected portions of the engaging member by the fast block and FIG. 15(B) is a schematic illustrating a fastened state of the projected portions of the engaging member by the fast block according to another embodiment.

In the above embodiments, the description has been carried out by adopting three engaging members 131 and fast block 132*b* having a substantially triangular shape, but it is not limited thereto. For example, as illustrated in FIG. 15(A) and FIG. 15(B), it is possible to adopt a fast block 133*d* which, as a whole, is formed into a shape of a race track having a curved surface portion 133*e* and a linear portion 133*d* which is configured to include a pair of D-cut surfaces each having a flat face on a part of the peripheral surface of a circular block, and two engaging members 131. The shape and the structure of engaging members 131 are the same as engaging members 131 illustrated in FIGS. 4 and 5 except that three engaging members 131 are replaced by two engaging members 131.

In the state illustrated in FIG. 15(A), a gap is formed between projected portions 131*a* and fast block 133*b*. In the case where an external force is applied from the external side to projected portions 131*a* in the radial direction, projected portions 131*a* displace toward the central portion into the retracted state in which projected portions 131*a* do not project from the outer surface of cylindrical portion 111*b*.

As illustrated in FIG. 15(B), in the case where cylindrical portion 111*b* and projected portion 131*a* of engaging member 131 are rotated by a pitch of 90° relative to fast block 133*b*, two vertices P1 of curved surface portions 133*e* of fast block 133*b* come into contact with the inner side of projected portions 131*a*, and thereby, projected portions 131*a* are fastened in the projected state.

It should be understood that the embodiments disclosed herein have been presented for the purpose of illustration and description but not limited in all aspects. It is intended that the scope of the present invention is not limited to the description above but defined by the scope of the claims and encompasses all modifications equivalent in meaning and scope to the claims.

REFERENCE SIGNS LIST

1: syringe; 2: piston; 2*a*: piston rubber; 2*b*: piston core; 10: pressure jacket; 111*b*: cylindrical portion; 20: piston-side engaging region; 21: first engaging wall region; 22: second engaging wall region; 100: injector head; 101: housing; 102: front plate; 103: spacer rod; 104: end plate; 104*h*: slide hole; 105: base block; 106: plunger forward-backward movement controlling servo motor; 107: ball screw; 107*a*: screw shaft; 107*b*: nut; 110: plunger; 111: outer cylinder; 111*a*: groove; 111*c*: window region, 111*g*: rack gear; 112: slider; 113: fast pin; 120: connection-control stepping motor; 121: pinion gear; 122: holding plate; 123: spacer; 124, 125: screw; 130: plunger-side engaging region; 131: engaging member; 131*a*: projected portion; 131*b*: extended portion; 131*c*: base portion; 132: fast member; 132, 132*a*: fast plate; 132*b*, 133*b*: fast block; 133*d*: linear portion (D-cut surface); 133*e*: curved surface portion; 134: fast ring; 135: screw

The invention claimed is:

1. A joint mechanism for a slidable plunger disposed in an injector head and a piston which is disposed inside a syringe mounted on said injector head, comprising:
   a plunger-side engaging region, which engages with said piston, being disposed at a proximal end of said plunger; and
   a piston-side engaging region, which engages with said plunger-side engaging region, being a hollow region inside said piston, wherein
      said piston-side engaging region comprises a bottom wall at a proximal end of said piston-side engaging region, an opening at a distal end of said piston-side engaging region, and a side wall extending between said bottom wall and said opening,
   said piston-side engaging region includes
      a first engaging wall region located on said side wall towards said opening of said piston-side engaging region and having a first inner diameter, and
      a second engaging wall region located on said side wall towards said bottom wall and adjacent to said first engaging wall region and having a second inner diameter greater than said first inner diameter, said plunger-side engaging region includes
      a cylindrical portion having an outer diameter smaller than said first inner diameter,
      an engaging member disposed inside said cylindrical portion, said engaging member includes
         a projected portion projecting from an outer surface of said cylindrical portion in a projected state and retracting from the outer surface of said cylindrical portion in a retracted state, said projected portion is switchable between said projected state and said retracted state,
         an extended portion extending from said projected portion in an axial direction of said cylindrical portion, and
         a base portion disposed at a side of said extended portion which is opposite to said projected portion,
         three said base portions are formed into a circular shape by combining three said base portions of three said engaging members together and having a fast ring disposed around outer peripheral surfaces of said base portions, and
      a fast block for fastening said engaging member in said projected state, said fast block being disposed inside said cylindrical portion and positioned closer towards a central portion thereof than said engaging member,
   in the case where said plunger and said piston are in a connected state, said fast block preventing said engaging member from moving toward the central portion in a radial direction so as to fasten said engaging member in said projected state, and
   in the case where said plunger and said piston are in a disconnected state, said fast block allowing said engaging member to move toward the central portion in the radial direction.

2. The joint mechanism according to claim 1, wherein said fast block is formed into a shape of a substantially equilateral triangle,
said engaging member is disposed on a peripheral surface of said cylindrical portion at three locations with a pitch of 120°, and is configured to be rotatable around said fast block together with said cylindrical portion,
said projected state of said engaging member is fastened at a position where three vertices of the triangle of said fast block come into contact with an inner side of said engaging member, and
the fastening of said projected state of said engaging member is released at a position where said engaging member is rotated by 60° to disengage said three vertices of the triangle of said fast block from the inner side of said engaging member.

* * * * *